United States Patent
Stroefer et al.

(10) Patent No.: US 7,345,207 B2
(45) Date of Patent: Mar. 18, 2008

(54) PRODUCTION OF HIGH-CONCENTRATION FORMALDEHYDE SOLUTIONS

(75) Inventors: Eckhard Stroefer, Mannheim (DE); Neven Lang, Mannheim (DE); Hans Hasse, Kaiserslautern (DE); Thomas Grützner, Stuttgart (DE); Michael Ott, Neckargemünd (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 106 days.

(21) Appl. No.: 10/547,732

(22) PCT Filed: Mar. 4, 2004

(86) PCT No.: PCT/EP2004/002180

§ 371 (c)(1),
(2), (4) Date: May 11, 2006

(87) PCT Pub. No.: WO2004/078678

PCT Pub. Date: Sep. 16, 2004

(65) Prior Publication Data

US 2006/0211841 A1  Sep. 21, 2006

(30) Foreign Application Priority Data

Mar. 4, 2003 (DE) ................. 103 09 289

(51) Int. Cl.
*G07C 45/78* (2006.01)
*C08G 8/04* (2006.01)

(52) U.S. Cl. ................. 568/470; 568/493; 528/129

(58) Field of Classification Search ............... None
See application file for complete search history.

(56) References Cited

U.S. PATENT DOCUMENTS

2004/0097762 A1   5/2004   Hoffmockel et al.

FOREIGN PATENT DOCUMENTS

| DE | 100 62 814 A1 | 6/2002 |
| GB | 1190682 | 3/1968 |

*Primary Examiner*—Sikarl A. Witherspoon
(74) *Attorney, Agent, or Firm*—Connolly Bove Lodge & Hutz LLP

(57) ABSTRACT

Process for preparing high-concentration formaldehyde solutions having a $CH_2O$ content of $\geq 50\%$ by weight from an aqueous formaldehyde solution having a lower $CH_2O$ content by evaporation of part of this solution (partial evaporation), in which the aqueous formaldehyde solution is heated to an evaporation temperature T at which the gas phase becomes enriched in water relative to the liquid phase and the gas phase formed is taken off continuously or discontinuously, wherein the evaporation temperature T obeys the relationship:

$$T[°C.] < T_{max}[°C.]$$

where $T_{max}(c) = A + B \times (c/100) + C \times (c/100)^2 + D \times (c/100)^3$ and
A=+68.759, B=+124.77, C=−12.851, D=−10.095,
where c is the instantaneous $CH_2O$ content of the aqueous formaldehyde solution during the evaporation in percent by weight and is from 20 to 99% by weight.

20 Claims, 2 Drawing Sheets

PRODUCTION OF HIGH-CONCENTRATION FORMALDEHYDE SOLUTIONS

This application is a National Stage of PCT/EP2004/002180 filed Mar. 4, 2004 which in turn claims priority from German Application 103 09 289.7, filed Mar. 4, 2003.

The invention relates to a process for preparing high-concentration formaldehyde solutions.

Formaldehyde is an important industrial chemical and is used to produce numerous industrial products and consumer articles. Over 50 branches of industry at present make use of formaldehyde, essentially in the form of aqueous solutions or formaldehyde-containing synthetic resins. Commercially available aqueous formaldehyde solutions have total concentrations of from 20 to 55% by weight of formaldehyde in the form of monomeric formaldehyde, methylene glycol and oligomeric polyoxymethylene glycols.

Water, monomeric (free) formaldehyde, methylene glycol and oligomeric polyoxymethylene glycols having various chain lengths are present together in aqueous solutions in a thermodynamic equilibrium which is characterized by a particular distribution of polyoxymethylene glycols of differing lengths. The term "aqueous formaldehyde solution" also refers to formaldehyde solutions in which virtually no free water is present essentially only in chemically bound form as methylene glycol or in the terminal OH groups of the polyoxymethylene glycols. This is particularly true of concentrated formaldehyde solutions. Polyoxymethylene glycols can have, for example, from 2 to 9 oxymethylene units. Thus, dioxymethylene glycol, trioxymethylene glycol, tetraoxymethylene glycol, pentaoxymethylene glycol, hexaoxymethylene glycol, heptaoxymethylene glycol, octaoxymethylene glycol and nonaoxymethylene glycol can be present together in aqueous formaldehyde solutions. The distribution is concentration-dependent. Thus, the maximum of the distribution in dilute formaldehyde solutions corresponds to homologues having a short chain length, while in more concentrated formaldehyde solutions it corresponds to homologues having a greater chain length. A shift in the equilibrium toward longer-chain (higher molecular weight) polyoxymethylene glycols can be brought about by removal of water, for example by simple distillation in a film evaporator. The establishment of equilibrium in this case occurs at a finite rate by intermolecular condensation of methylene glycol and low molecular weight polyoxymethylene glycols with elimination of water to form higher molecular weight polyoxymethylene glycols.

However, the high-concentration formaldehyde solutions obtained by removal of water are unstable in the sense that precipitation of solids occurs after a certain time. The precipitated solids are essentially the above-described longer-chain formaldehyde oligomers or polyoxymethylene glycols. It is known that moderately concentrated formaldehyde solutions having $CH_2O$ contents of up to about 50% by weight can be mixed with about 0.2-2% by weight of methanol as stabilizer and be stored at about 55° C. to avoid precipitation of solids. More highly concentrated formaldehyde solutions having a $CH_2O$ content of >70% by weight, for example about 80% by weight, initially consist of a single phase after their preparation at low temperatures of about 20-50° C. However, precipitation of solids occurs after a certain time. The cause appears to be the growth of the polyoxymethylene glycol chains in the formaldehyde solution until the solubility limit is exceeded.

It is an object of the present invention to provide a process for preparing high-concentration aqueous formaldehyde solutions having a $CH_2O$ content of ≧50% by weight, in which precipitation of solids is either avoided completely or occurs to only a minor extent. In any case, the precipitation of solids should be sufficiently small for the resulting suspension to be able to be conveyed in industrial apparatuses. In general, this is the case when the solids content is up to 10% by weight.

We have found that this object is achieved by a process for preparing high-concentration formaldehyde solutions having a $CH_2O$ content of ≧50% by weight from an aqueous formaldehyde solution having a lower $CH_2O$ content by evaporation of part of this solution (partial evaporation), in which the aqueous formaldehyde solution is heated to an evaporation temperature T at which the gas phase becomes enriched in water relative to the liquid phase and the gas phase formed is taken off continuously or discontinuously, wherein the evaporation temperature T obeys the relationship:

$$T[° C.] < T_{max}[° C.]$$

where $T_{max}(c) = A + B \times (c/100) + C \times (c/100) + D \times (c/100)^3$ and

A=+68.759, B=+124.77, C=−12.851, D=−10.095, where c is the instantaneous $CH_2O$ content of the aqueous formaldehyde solution during the evaporation in percent by weight and is from 20 to 99% by weight.

Preference is given to using an aqueous formaldehyde solution having a $CH_2O$ content of from 10 to 95% by weight, particularly preferably from 30 to 85% by weight, as starting material. This can be obtained by oxidatively dehydrogenating methanol and, if desired, subsequently concentrating the aqueous formaldehyde solution obtained. The process of the present invention enables high-concentration formaldehyde solutions having a $CH_2O$ content of >80% or even from >95% by weight to 99% by weight to be obtained.

The evaporation can be carried out in commercial apparatuses. Examples of suitable apparatuses are stirred vessels which can be heated, for example, by means of jackets or coiled tubes (internal or external). Apparatuses having heat exchanger characteristics, e.g. shell-and-tube heat exchangers, plate apparatuses or helically bound tubes, are particularly useful. These can be operated in cocurrent, counter-current or cross-current. Heating can be carried out by means of any media, for example using condensing steam or by means of single-phase liquids or gases. Evaporation of the aqueous formaldehyde solution can be carried out in a single pass through the evaporator or with circulation. If, in particular, complete evaporation is sought, a single pass of the formaldehyde solution through the evaporator will generally not be sufficient.

Evaporation can also be carried out in a column, for example a bubble cap tray column.

The formaldehyde solution is preferably evaporated at a temperature at which no solid precipitates. Particular preference is given to maintaining a temperature at which no solid precipitates at every point in the evaporator. For example, this temperature is maintained both in the evaporator itself and, when the evaporator is operated with circulation, in the circuit through which circulation occurs and, when the aqueous formaldehyde solution is taken off, in the facilities downstream of the evaporator.

For this purpose, a temperature which obeys the relationship $$T[° C.] > T_{min}[° C.]$$

where $T_{min}(c) = A' + B' \times (c/100) + C' \times (c/100)^2 + D' \times (c/100)^3$ and where A'=+6.0156, B'=+52.918, C'=+49.699, D'=+34.286, where c is the instantaneous CH$_2$O content of the aqueous formaldehyde solution during evaporation in percent by weight and is from 20 to 99% by weight, is maintained in the aqueous formaldehyde solution at every point in the evaporator.

It has surprisingly been found that aqueous formaldehyde solutions can be concentrated by partial evaporation without precipitation of solids occurring when evaporation is carried out within the above-defined temperature window.

The decrease in the water content of the liquid phase can be explained by water being liberated as a result of condensation of polyoxymethylene glycols with one another or of polyoxymethylene glycols with methylene glycol.

The evaporation of the aqueous formaldehyde solution can be carried out in the presence of acidic or basic catalysts which catalyze the condensation reactions outlined above. However, for cost reasons and also to avoid deposits on the heat exchanger surfaces, the additions of catalyst should be kept small. Catalysis can be carried out homogeneously or heterogeneously in a suspension or fixed-bed mode.

In general, the pressure during the partial evaporation is in the range from 0.02 to 50 bar, preferably in the range from 0.1 to 17 bar.

The partial evaporation can be carried out continuously or batchwise. In a batchwise mode of operation, the partial evaporation is carried out, for example, in a simple stirred vessel. The partial evaporation can also be carried out continuously in a film evaporator or thin film evaporator, as described in EP-A 1 063 221, or in a helical tube evaporator, as described in DE-A 27 19 967.

The process of the present invention preferably starts out from moderately concentrated or highly concentrated formaldehyde solutions having a CH$_2$O content of from 30 to 95% by weight which have been stabilized against precipitation of solids as described below after they have been prepared.

Relatively highly concentrated formaldehyde solutions containing, for example, >70% by weight of CH$_2$O are initially obtained as a single phase in the preparation at low temperatures of from about 20 to 50° C. However, precipitation of solids occurs after a certain time. The cause appears to be growth of the polyoxymethylene glycol chains in the formaldehyde solution until the solubility limit is exceeded. The solutions can be stabilized against precipitation of solids by heating them at a heating rate of at least 5° C./min to a temperature of from 80° C. to 200° C. immediately after they have been prepared and leaving them at a temperature in this range. "Immediately after they have been prepared" means that the high-concentration formaldehyde solutions obtained at, for example, from 20 to 60° C. are heated at the specified heating rate after not more than 60 minutes, preferably after not more than 5 minutes.

The heating rate is preferably at least 10° C./min. A heating rate of at least 10° C./min is preferred particularly when the pH of the solution is <3 or >6. The solution is preferably heated at the specified heating rate to at least 100° C. and the temperature subsequently does not go below this value. The pH of the high-concentration formaldehyde solution is usually in the range of from 1 to 10, preferably from 2 to 9, particularly preferably from 3 to 6. The pH can be brought into the desired range by addition of buffer substances, for example a formate buffer.

Stabilization and evaporation of the high-concentration aqueous formaldehyde solutions are preferably carried out in one apparatus.

The high-concentration formaldehyde solutions obtained can be used for a large number of chemical reactions. Examples of such reactions are the reaction of acetylene with formaldehyde solution in a Reppe reaction to form butynediol which can be hydrogenated to give butanediol;

aldolization reactions of formaldehyde with itself or with higher aldehydes to form polyhydric alcohols and sugars, pentaerythritol, trimethylolpropane and neopentyl glycol;

the reaction of formaldehyde and CO to give glycolic acid;

the preparation of chelating substances such as glycol nitrites from solutions of formaldehyde;

the reaction of formaldehyde with olefins in a Prins reaction to give alpha-hydroxymethyl compounds;

condensation reactions of formaldehyde with amines such as aniline or toluidine to form Schiff bases which can react further to give diphenylmethane derivatives such as diphenylmethanediamine;

reaction of hydroxylamine with formaldehyde to form oximes;

reaction of formaldehyde with diols to form cyclic ethers, for example of glycol and formaldehyde to form dioxolane.

This listing is not exhaustive. Textbooks on organic chemistry and industrial chemistry give further examples of reactions. However, the listing is intended to illustrate, by way of example, the industrial importance of formaldehyde as a synthetic building block in the overall field of organic chemistry. The products obtained include both small tonnage intermediates in the pharmaceuticals or crop protection sectors, e.g. oximes, and large tonnage products such as diphenylmethane derivatives.

The high-concentration formaldehyde solution prepared according to the present invention is particularly preferably used for preparing polyoxymethylene plastics. The preparation of polyoxymethylene plastics is described, for example, in the German patent application DE 101 58 813.5, which is not a prior publication. The use of the high-concentration formaldehyde solution for preparing trioxane or tetraoxane in the liquid phase is also preferred. Preference is also given to using the high-concentration formaldehyde solution for preparing polyoxymethylene dialkyl ethers by condensation with alcohols.

Figure 1:
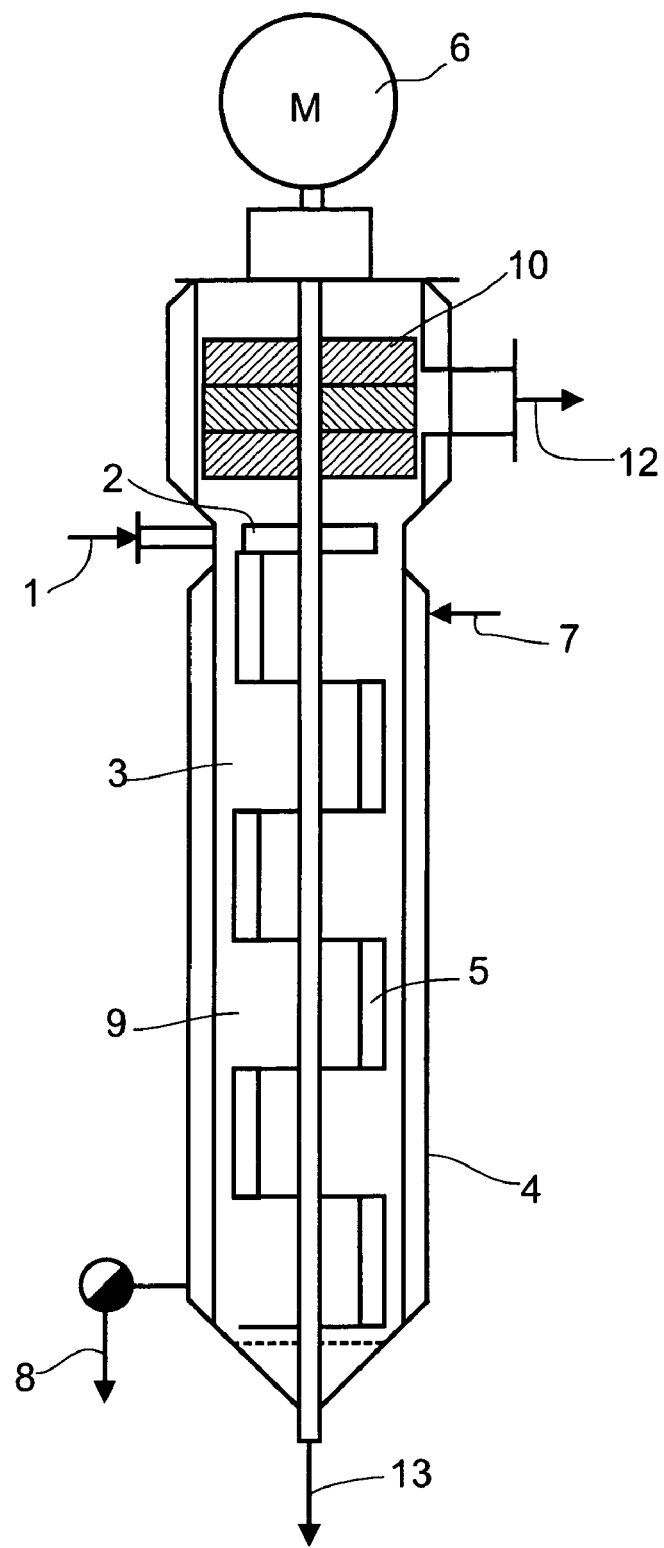
FIGS. 1 and 2 illustrate apparatus suitable for carrying out the present invention.
Figure 2:
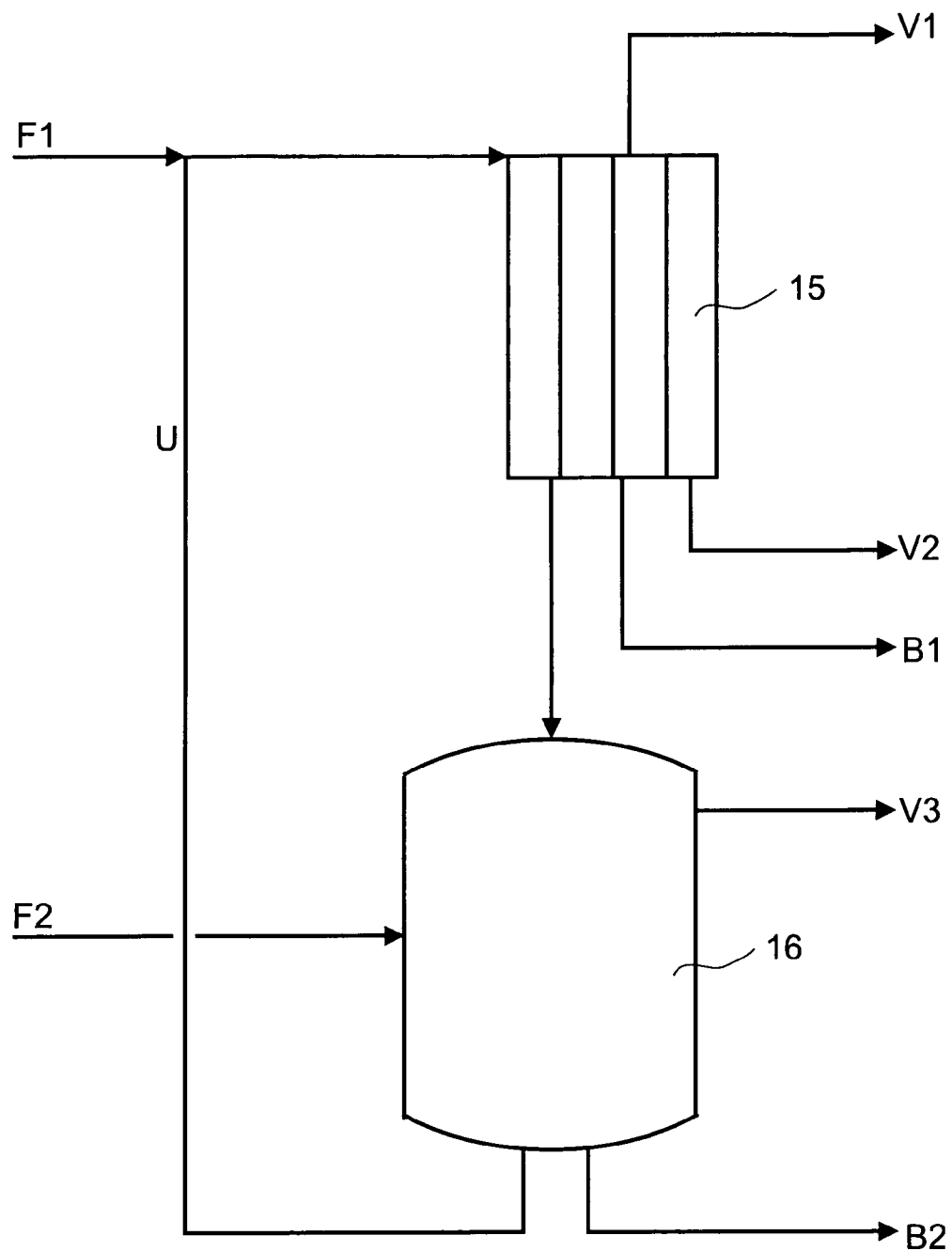

The invention is illustrated by the following examples.

EXAMPLES

Example 1

In a laboratory experiment, a high-concentration formaldehyde solution is prepared in a thin film evaporator in a single pass. The evaporator has an evaporation area of 0.092 m$^2$ and a length of 1.1 m. A 48% strength by weight aqueous formalin solution is introduced at the top. The flow rate is 615 g/h. The wall temperature is 90° C. and the pressure is 80 mbar. At the bottom, 298 g/h of a high-concentration formaldehyde solution having a concentration of 84% by weight are taken off. 321 g/h of vapor are taken off at the top. The solution from the bottom is conveyed by means of a laboratory pump into a heated standard laboratory stirred reactor having a capacity of 1 l. The reactor is maintained at an internal temperature of 130° C. A liquid stream of 64 g/h is taken off from the reactor. A gas stream of 234 g/h is taken off from the gas phase of the reactor. According to analysis, the liquid stream contains a 85.1% by weight of formaldehyde, calculated as $CH_2O$.

Example 2

In a laboratory experiment, a high-concentration formaldehyde solution is worked up in a distillation column. The column is a bubble cap tray column having 20 theoretical plates and an internal diameter of 50 mm. The pressure at the top of the column is 2.0 bar.

A formaldehyde solution containing 84% by weight of formaldehyde is introduced into the column on the tenth theoretical plate. The flow rate is 2.8 kg/h, and the temperature is 107° C. 0.93 kg/h is taken off at the top of the column. The formaldehyde content of the stream taken off at the top is 77.2% by weight. At the bottom of the column, 1.85 kg/h of a more concentrated solution having a formaldehyde content of 87.3% by weight are taken off. The temperature of the stream taken off at the bottom is 122° C.

We claim:

1. A process for preparing high-concentration formaldehyde solutions having a $CH_2O$ content of $\geq 50\%$ by weight from an aqueous formaldehyde solution having a lower $CH_2O$ content by evaporation of part of this solution (partial evaporation), in which the aqueous formaldehyde solution is heated to an evaporation temperature T at which the gas phase becomes enriched in water relative to the liquid phase and the gas phase formed is taken off continuously or discontinuously, wherein the evaporation temperature T obeys the relationship:

$$T[°C.] < T_{max}[°C.]$$

where $T_{max}(c) = A + B \times (c/100) + C \times (c/100)^2 + D \times (c/100)^3$ and

A=−68.759, B=−124.77, C=−12.851, D=−10.095, wherein a temperature which obeys the relationship $$T[°C.] > T_{min}[°C.]$$

where $T_{min}(c) = A' + B' \times (c/100) + C' \times (c/100)^2 + D' \times (c/100)^3$ and where A'=+6.0156, B'=+52.918, C'=+49.699, D'=+34.286, is maintained in the aqueous formaldehyde solution at every point in the evaporator, where c is the instantaneous $CH_2O$ content of the aqueous formaldehyde solution during the evaporation in percent by weight and is from 20 to 99% by weight.

2. A process as claimed in claim 1, wherein the aqueous formaldehyde solution used as starting material in the process has a $CH_2O$ content of from 10 to 95% by weight.

3. A process as claimed in claim 2, wherein the aqueous formaldehyde solution used as starting material in the process has a $CH_2O$ content of from 30 to 85% by weight.

4. A process as claimed in claim 1, wherein the pressure during the partial evaporation is from 0.1 to 50 bar.

5. A process as claimed in claim 1, wherein the high-concentration formaldehyde solution obtained has a $CH_2O$ content of from 50 to 99% by weight.

6. A process as claimed in claim 1, wherein the evaporation of the aqueous formaldehyde solution is carried out in a stirred vessel, a helically wound tube, a film evaporator or another apparatus having heat exchanger characteristics.

7. A process as claimed in claim 1, wherein the aqueous formaldehyde solution used as starting material for the process is prepared by oxidative dehydrogenation of methanol.

8. A process as claimed in claim 2, wherein the pressure during the partial evaporation is from 0.1 to 50 bar.

9. A process as claimed in claim 3, wherein the pressure during the partial evaporation is from 0.1 to 50 bar.

10. A process as claimed in claim 2, wherein the high-concentration formaldehyde solution obtained has a $CH_2O$ content of from 50 to 99% by weight.

11. A process as claimed in claim 3, wherein the high-concentration formaldehyde solution obtained has a $CH_2O$ content of from 50 to 99% by weight.

12. A process as claimed in claim 4, wherein the high-concentration formaldehyde solution obtained has a $CH_2O$ content of from 50 to 99% by weight.

13. A process as claimed in claim 2, wherein the evaporation of the aqueous formaldehyde solution is carried out in a stirred vessel, a helically wound tube, a film evaporator or another apparatus having heat exchanger characteristics.

14. A process as claimed in claim 3, wherein the evaporation of the aqueous formaldehyde solution is carried out in a stirred vessel, a helically wound tube, a film evaporator or another apparatus having heat exchanger characteristics.

15. A process as claimed in claim 4, wherein the evaporation of the aqueous formaldehyde solution is carried out in a stirred vessel, a helically wound tube, a film evaporator or another apparatus having heat exchanger characteristics.

16. A process as claimed in claim 5, wherein the evaporation of the aqueous formaldehyde solution is carried out in a stirred vessel, a helically wound tube, a film evaporator or another apparatus having heat exchanger characteristics.

17. A process as claimed in claim 2, wherein the aqueous formaldehyde solution used as starting material for the process is prepared by oxidative dehydrogenation of methanol.

18. A process as claimed in claim 3, wherein the aqueous formaldehyde solution used as starting material for the process is prepared by oxidative dehydrogenation of methanol.

19. A process as claimed in claim 4, wherein the aqueous formaldehyde solution used as starting material for the process is prepared by oxidative dehydrogenation of methanol.

20. A process as claimed in claim 5, wherein the aqueous formaldehyde solution used as starting material for the process is prepared by oxidative dehydrogenation of methanol.

* * * * *